United States Patent
Schwartz et al.

(10) Patent No.: US 6,878,668 B1
(45) Date of Patent: Apr. 12, 2005

(54) PROCESS FOR MANUFACTURE OF AN ATTRITION RESISTANT CATALYST

(75) Inventors: Jo-Ann T. Schwartz, Chadds Ford, PA (US); Dwain T. Cline, Jr., North East, MD (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 607 days.

(21) Appl. No.: 09/613,698

(22) Filed: Jul. 11, 2000

Related U.S. Application Data

(60) Provisional application No. 60/143,667, filed on Jul. 14, 1999.

(51) Int. Cl.$^7$ .............................. B01J 21/08; B01J 23/22
(52) U.S. Cl. .......................... 502/247; 502/8; 502/209; 502/504
(58) Field of Search ............................... 502/247, 248, 502/255, 305, 353, 504, 8

(56) References Cited

U.S. PATENT DOCUMENTS

| | | | | |
|---|---|---|---|---|
| 4,127,591 A | * | 11/1978 | Kamimura | .................. 549/260 |
| 4,317,778 A | * | 3/1982 | Blum et al. | ............. 260/346.75 |
| 4,351,773 A | * | 9/1982 | Milberger | .................... 549/259 |
| 4,677,084 A | | 6/1987 | Bergna | ........................... 502/8 |
| 4,769,477 A | | 9/1988 | Bergna | ........................ 549/259 |
| 5,128,114 A | * | 7/1992 | Schwartz | ..................... 423/335 |
| 5,302,566 A | | 4/1994 | Schwartz | ........................ 502/8 |
| 6,107,238 A | * | 8/2000 | Contractor et al. | ......... 502/247 |

OTHER PUBLICATIONS

U.S. Appl. No. 09/163,680 filed Sep. 30, 1998.
U.S. Provisional Application 06/109,403 filed Nov. 20, 1998.

* cited by examiner

Primary Examiner—Ngoc-Yen Nguyen

(57) ABSTRACT

A method for manufacturing of an attrition resistant vanadium/phosphorous oxide catalyst involving forming an aqueous slurry comprising; vanadium/phosphorous oxide catalyst or vanadium/phosphorous oxide catalyst precursor particles, an aqueous solution of $H_3PO_4$, and optionally an aqueous colloidal silica sol, an aqueous polysilicic acid solution or mixture thereof and then spray drying the slurry to form attrition resistant catalyst precursor followed by calcining/activating the spray dried precursor. Such a catalyst is particularly useful in oxidation processes such as the catalytic air oxidation of butane to maleic anhydride.

1 Claim, No Drawings

PROCESS FOR MANUFACTURE OF AN ATTRITION RESISTANT CATALYST

CROSS REFERENCE TO RELATED APPLICATION

Benefit of priority is being claimed from the Provisional Application 60/143,667 filed Jul. 14, 1999.

BACKGROUND OF THE INVENTION

1. Field of the Invention

This invention relates a process for preparing an attrition resistant catalyst. More specifically, but not by way of limitation, the invention relates to a method of imparting attrition resistance to a particulate catalyst or catalyst precursor (e.g., vanadium/phosphorus oxide, V/P/O, solids) by spray drying a slurry containing catalyst or catalyst precursor and optionally a large size silica colloidal sol, polysilicic acid or mixtures thereof in the presence of $H_3PO_4$ followed by calcining the spray dried product.

2. Description of the Related Art

The use of inert metal oxides such as silica or the like as a support for catalysts or as a binder for catalyst particles is generally well known in the art. In particular, U.S. Pat. No. 4,677,084 discloses and claims a process for producing attrition resistant catalyst or catalyst support particles having an oxide-rich surface layer as well as claims the attrition resistant particles. In a divisional U.S. Pat. No. 4,769,477 the use of attrition resistant vanadium/phosphorus oxide catalyst particles (made by the above process) having a $SiO_2$-rich surface layer for producing maleic anhydride by oxidation of a hydrocarbon is similarly disclosed and claimed. The method of producing the attrition resistant catalyst particles according to these patents involves the forming of a slurry of catalyst, catalyst precursor or catalyst support particles in a solution containing a solute consisting essentially of the oxide precursor particle (i.e., that which becomes or forms the resulting oxide-rich surface layer; e.g., silicic acid, polysilicic acid or the like). This oxide precursor particle useful in this process is characterized by an average particle size no greater than 5 nanometers and the relative amount of the same is chosen such that the weight of the oxide to be formed as a surface layer is about 3 to 15 percent of the total weight of the resulting attrition resistant particles. This slurry is then spray dried to form porous microspheres which are then calcined to produce attrition resistant catalyst. Both of these patents further contain extensive background reviews of relevant prior patent references and the present invention can be viewed as a further improvement relative to each. As such, U.S. Pat. Nos. 4,677,084 and 4,769,477 are incorporated herein by reference for disclosure purposes.

U.S. Pat. No. 5,302,566 discloses an alternate method for preparing an attrition resistant catalyst described above, particularly vanadium/phosphorus oxide catalyst, having an oxide-rich surface layer. In this alternative method the slurry to be spray dried comprises the catalyst or catalyst precursor particles and a mixture of a solution containing a solute consisting essentially of the oxide precursor particles of less than 5 nm along with a colloidal oxide sol wherein the oxide sol particles have an average size of between 5 and 7 nm. The amount of colloidal oxide sol is selected such as to provide between 50 to 95 percent by weight of the final oxide-rich surface and the polysilicic acid provides 50 to 5 percent. Again, the oxide-rich surface is between 3 and 15 percent by weight of the total weight of resulting attrition resistant catalyst. The resulting catalyst made by this alternative process is shown to be comparable in attrition resistance properties to a catalyst made using only oxide precursor solution as the surface forming oxide source. The mixture of combined oxide precursor solution and 5 to 7 nm colloidal sol, however, is significantly more stable than a solution of oxide precursor alone. Consequently, advantages in terms of shelf-life, storage, and handling are realized particularly when scaling up to commercial production levels. U.S. Pat. No. 5,302,566 is incorporated herein by reference for disclosure purposes.

In a copending and commonly assigned U.S. patent application Ser. No. 09/163,680 filed Sep. 30, 1998, now U.S. Pat. No. 6,107,238, incorporated herein by reference, a further improvement relating to the above described processes is disclosed. In this process the colloidal oxide sol employed has an average size between 10 and 100 nm and the amount used is selected such that from 25 to 50 percent of the resulting weight of attrition resistant catalyst is derived from the colloidal oxide sol. The soluble solute component (e.g., the silicic acid or polysilicic acid) in the slurry prior to spray drying again is characterized by an average particle size no greater than 5 nm and the amount employed is selected such that from 5 to 15 percent of the weight of the attrition resistant catalyst (including the colloidal sol contribution) is derived from the soluble oxide precursor. This particular process and resulting attrition resistant catalyst is intended to alleviate a specific problem associated with transition metal oxide containing catalysts that can expand and shrink during the oxidation and reduction cycles associated with continuous use and the associated increase attrition losses observed during the reduced state.

BRIEF SUMMARY OF THE INVENTION

In view of the above prior art, it has now been discovered that an attrition resistant vanadium/phosphorous oxide catalyst can be prepared by intentionally employing phosphoric acid, $H_3PO_4$, or the like in the aqueous slurry containing vanadium/phosphorous oxide catalyst or catalyst precursor particles to be spray dried. Optionally a large size silica colloidal sol, polysilicic acid or mixtures thereof may be advantageously present in the aqueous slurry prior to spray drying in the presence of $H_3PO_4$. The spray dried solids are then calcined and activated as generally known it the art.

Thus the present invention provides a process for manufacture of an attrition resistant vanadium/phosphorous oxide catalyst comprising the steps of:
a) forming a slurry comprising;
  i) vanadium/phosphorous oxide catalyst or vanadium/phosphorous oxide catalyst precursor particles,
  ii) aqueous $H_3PO_4$ solution, and
  iii) optionally an aqueous colloidal silica sol, an aqueous polysilicic acid solution or mixture thereof;
b) spray drying the slurry from step (a) to form attrition resistant catalyst precursor soilids; and
c) calcining the spray dried solids of step (b) to produce attrition resistant catalyst.

DETAILED DESCRIPTION OF THE INVENTION

The process of the present invention is technologically related to the process described in U.S. Pat. Nos. 4,677,084; 4,769,477 and 5,302,566 and consequently the full disclosure of each is incorporated herein by reference for disclosure purposes. The process of the present invention is also technologically related to the process described in co-pending and commonly assigned U.S. Provisional Pat. Application No. 60/109,403 filed Nov. 20, 1998 and consequently the full disclosure of this provisional application is incorporated herein by reference for disclosure purposes. As set forth in the above three published patents, the small particle size of the oxide precursor in solution (i.e., no greater than 5 nm) is important during the spray drying of the slurry in that it enables the oxide precursor to flow to the peripheral region of the porous microsphere being formed. The small particle size is also identified as being important in producing the hard peripheral oxide-rich outer shell or surface layer responsible for the attrition resistance. As described in the U.S. Pat. Nos. 4,677,084 and 4,769,477 issued to Bergna, when this oxide precursor is an aqueous silicic acid or polysilicic acid solution of particle size no greater than 5 nm which is spray dried at for example 10 weight percent $SiO_2$ loading with a vanadium/phosphorus oxide catalyst precursor and then calcined at typically 400° C. for 1 hour an attrition resistant porous microsphere will be achieved. These three references further teach that the particles of silica 2 to 6 nm in diameter sinter together to some extent even under the temperature conditions encountered in a conventional spray drying process, whereas particles 10 to 100 nm do not sinter below 700 to 1,000° C. As a result, attrition resistance of the catalyst, catalyst precursor or support particle is a function of the particle size and degree of aggregation of the silica formed by dehydration during spray drying.

In view of the fact that particles of silica 2 to 3 nm in diameter, such as those present in polysilicic acid solution, form hard shells on the resulting porous microspheres under conventional spray drying conditions, the U.S. Pat. Nos. 4,677,084 and 4,769,477 acknowledge and define the concept of "green" attrition resistant; i.e., the attrition resistance before calcination of the porous microshere. It is further taught that the green attrition resistance before calcination of a vanadium/phosphorus oxide catalyst precursor with 10 weight percent $SiO_2$ shell prepared by using polysilicic acid is as high as the attrition resistance of these microspheres after calcination at 400° C. for 1 hour. These references further note that calcination of the vanadium/phosphorus oxide precursor microspheres is necessary to convert the precursor to the catalyst and, since the green attrition resistance is so high, calcination can be carried out when convenient, for example, when the microspheres are in the reactor. It is further indicated that the green attrition resistance of the porous microspheres of vanadium/phosphorus oxide catalyst precursor with 10 wt % $SiO_2$ shell is significantly lower when a colloidal sol of particles of 5 nm is used as the source of the silica instead of polysilicic acid. Also, when a colloidal sol of particles of 14 nm diameter is used as the source of the silica, the green attrition resistance is even lower. When a colloidal sol of particles of 22 nm diameter is used as the source of the silica, significant green attrition resistance is not realized even when the amount of silica is increased to 20 wt %. Furthermore, calcination of the porous microspheres of vanadium/phosphorus oxide catalyst precursor with 10 wt % $SiO_2$ does not result in adequate attrition resistance when the silica particle diameter in the silica source exceeds 5 nm.

In U.S. Pat. No. 5,302,566 an alternate process for preparing an attrition resistant catalyst similar to the process of the U.S. Pat. Nos. 4,677,084 and 4,769,477 is disclosed. In this improvement the vanadium/phosphorus oxide catalyst having an $SiO_2$ surface layer is obtained from a stable silica forming mixture which contains both a colloidal silica sol and a soluble silica forming precursor solution. More specifically, the improved process involves the use of a colloidal oxide sol containing particles of average diameter of 5 to 7 nm in combination with the soluble silica precursor such as silicic acid or polysilicic acid. Again, a mixture of the silica forming agents are slurried with the catalyst or catalyst precursor particles and then the slurry is spray dried followed by calcination. The total oxide layer derived from the mixture of colloidal sol and polysilicic acid in the final catalyst is from 3 to 15 wt % of the attrition resistant catalyst.

The U.S. Pat. No. 5,302,566 teaches that up to 95% by weight of this oxide-rich surface may be derived from the colloidal sol and as little as 5% by weight from the polysilicic acid solution (i.e., the soluble silica). This reference again establishes that a catalyst wherein the oxide layer is derived entirely from colloidal silica (e.g. Ludox® FM; average particle size 5 nm) exhibits unsatisfactory attrition resistance. However, a catalyst wherein the oxide is derived from both colloidal silica and very little soluble silica exhibits a very desirable level of attrition resistance fully comparable to the attrition resistance associated with a catalyst prepared using entirely soluble silica. It was found that replacing 50 to 90% of the soluble silica (PSA) with colloidal silica results in formation of an essentially equivalent oxide shell which forms as the spray-dried droplets form the microspheres, provided the size of the particles in the colloidal sol is not greater than about 7 nm. The morphology of the resulting attrition resistant catalyst; i.e., the oxide being deposited as an outer shell, is similar to catalyst produced using soluble silica as the sole source of oxide.

The improvement associated with the U.S. Pat. No. 5,302,566 is related to the fact that the mixture containing colloidal sol and oxide precursor (PSA) solution is considerably more stable than the oxide precursor solution alone, which as noted in this patent, tends to rapidly gel. The stability of colloidal sol/PSA mixtures combined at different proportions ranging from 50/50 wt % to 95 wt % colloidal sol and 5 wt % PSA was assessed after storage for various time periods and was found to be comparable to that of freshly prepared PSA solutions. More specifically, a 95/5 w/w mixture of Ludox® FM/PSA, after 5 days storage, showed a viscosity profile very similar to that of a freshly prepared solution of 5% by weight PSA (stored 30 minutes), whereas the PSA solution gelled and was intractable after 22 hours of storage. Mixtures of Ludox® FM/PSA prepared at 70/30 and 50/50 proportions by weight, without added precursor particles, underwent no significant change in viscosity profile following storage for 71 hours. Thus the improvement addressed in the U.S. Pat. No. 5,302,566 dealt exclusively with an observed increase in stability of the mixtures of a 5 to 7 nm colloidal sol and polysilicic acid solution and the resulting distinct processing advantages relative to the use of a PSA solution alone, particularly when the respective processes are carried out on a large commercial scale.

In contrast to the processes disclosed in these previously published patents, the process of the above cited provisional application 60/109,403 involves the use of a colloidal sol wherein the average particle size is in excess of 10 nm in combination with the precursor solution of silicic acid, polysilicic acid or small diameter colloidal silica sol (less than 10 nm). In further contrast, the purpose and function of the intentional use of a colloidal sol of large particle dimensions (i.e., greater than 10 nm) is to improve the performance characteristics of the resulting attrition resistance catalyst relative to an attrition resistant catalyst prepared using PSA as the sole silica source. More specifically, the presence of the large diameter colloidal sol increases the resulting attrition resistant catalyst surface area, pore volume and pore size relative to an attrition resistant catalyst prepared using polysilicic acid as the sole silica source. The presence of the large particle size sol in combination with the polysilicic acid solution results in a stable mixture and thus all of the processing advantages associated with the U.S. Pat. No. 5,302,566 patented process are achieved and retained. However, the quantitative level of attrition resistance achieved in the instant invention relative to these previous processes is some what diminished at comparable silica surface layer loading, but the respective attrition resistance achieved is still commercially significant and operationally practical. The performance level of the vanadium/phosphorus oxide catalyst at 10 wt % $SiO_2$ of the instant process in the vapor phase oxidation of butane when compared to the corresponding attrition resistant catalyst made using only PSA, shows about a 40% increase in yield and conversion at comparable percent selectivity relative to the production of maleic anhydride. The incorporation of the large size colloidal sol particles in the mixture forming the silica surface layer thus tends to create a more open structure with higher surface area and pore volume in the resulting attrition resistant catalyst. This, in turn, alleviates any inherent diffusion limitations and improves intraparticle diffusion of reactants and products. Thus the process of the provisional application 60/109,403 leads to improved catalyst performance; albeit, at the partial expense of attrition resistance. However, it was found according to the provisional application 60/109,403 that any associated loss in attrition resistance can, in part, be minimized by employing a greater relative amount of PSA when a larger sol is being employed (e.g., 50 wt % PSA with 60 to 75 nm particle size) and more modest amounts of PSA when a diameter sol closer to about 10 nm particle size is being employed (e.g., 5 wt % PSA with 1.2 nm particle size).

In contrast to the above, the process of this invention provides for the intentional use of phosporic acid or an equivalent source of phosporic acid in the aqueous slurry prior to the slurry being spray dried to for catalyst percursor solids. According to the present invention, it has been discovered that the presence of $H_3PO_4$ during spray drying enhances and/or improves attrition resistance in the ultimate calcined/activated vanadium/phosphorus oxide catalyst being produced. This enhancement is observed in essentially all of the previously mentioned prior art catalyst preparation methods involving either a silica sol, silicic acid, polysilicic acid or combination thereof as the attrition resistant additive being combined with the vanadium/phosphorus oxide precursor solids. In fact and as demonstrated in the examples, it has now been found that the use of phosphoric acid in the slurry to be spray dried will contribute significant attrition resistance to the ultimate vanadium/phosphorus oxide catalyst even in the absence of a silica additive.

The catalyst or catalyst precursor useful in preparing the slurry to be spray dried can be any catalyst active solids suitable for vapor phase catalytic processes wherein attrition resistance is needed; for example; processes carried out in a recirculating solids reactor system, a transport bed reactor, fluidized bed reactor or even a fixed bed reactor. Similarly the catalyst support can be any particulate solids conveniently employed in a similar manner. The active ingredient in or on such catalysts, catalyst precursors and catalyst supports is typically a transition metal oxide or mixed oxide or any other oxides or mixed oxides; however, in the broadest application of the instant invention it can be any compatible agent. Of particular interest herein are vanadium, vanadium-phosphorus, multimetal molybdenum-vanadium and other vanadium-containing catalysts and the like that are conventionally known as the active catalytic ingredient for various vapor phase oxidation and ammoxidation reactions. Most particularly, the use of vadium/phosphorus oxide catalyzed air oxidation of butane for commercial production of maleic anhydride is of primary interest. For this reason, the following disclosure and examples will focus on preparation of an attrition resistant vanadium/phosphorus oxide catalyst precursor as representing a particularly preferred embodiment, but the invention is not limited thereto, and preparation of other catalysts used in other vapor phase catalytic reactions are contemplated as being benefited from the process improvements disclosed herein.

The catalyst or catalyst precursor particles used in preparing the slurry can be made or obtained by synthesis or by commuting larger particles. Typically the starting particles are of the order of 0.5 to about 10 $\mu$m in size and are to be reduced in size by micronization or similar size reduction process to a mean particle size of below about 3 microns, preferably below about 2 microns. It has been found that attrition resistance is sometimes unsatisfactory when particles much larger than 3 microns are used.

Preferably, both the colloidal oxide sol and the soluble oxide precursor must be chosen so that they have minimum or no deleterious effect on the catalytic performance of the particular catalyst being used. The oxides should be inert or show no catalytic activity for the particular chemical reaction being performed. Further, when an attrition resistant catalyst is being formed by spray during, the resulting peripheral oxide layer should not affect the behavior of the catalytically active phase during the subsequent calcination step and any activation steps. When either or both of these optional components are employed, the morphology of the resulting microspheres should be such that peripheral oxide layer allows the reactants access to the catalytically active phase. And, this oxide-rich surface layer should have no deleterious effect on catalyst performance.

The actual choice of oxide for the colloidal oxide sol can be made independently of the choice of oxide of the soluble oxide precursor provide the above compatibility and performance criteria are met. Preferably the same oxide is to be employed. Thus the oxide is generally any refractory oxide of the appropriate dimensions and compatibility which by way of example but not limitation includes $SiO_2$, $Al_2O_3$, $P_2O_5$, $TiO_2$, $ZrO_2$, MgO, rare earth oxides, and mixtures thereof. Most preferably, $SiO_2$ is to be employed.

The $SiO_2$ colloidal oxide sol can conveniently be any commercially available material, such as those available under the trade names Ludox® colloidal silica or Nalco® colloidal silica. Typically such commercially available solutions will contain a stabilizing counter ion such as the sodium or ammonium ion, which is preferably removed prior to use by contact with an acid ion exchange resin. A variety of such silicas with average particle sizes up to several 100 nm have been tested and found satisfactory.

The solvent used in the slurry to be spray dried is a solvent for the oxide precursor. Water is preferred. The solute consists essentially of an oxide precursor of subcolloidal particle size. "Subcolloidal particle size" is defined herein as that of particles for which the largest dimension is no greater than 5 nm. The solute particles must not agglomerate, precipitate or gel during or following the formation of the solution or in contact with the catalyst, catalyst precursor or catalyst support particles. The solute particles must provide a sufficiently stable solution and slurry to permit spray drying. Because the solute particles with the above properties are much smaller than the voids or spaces between the catalyst, catalyst precursor or catalyst support particles, and are even appreciably smaller than the colloid oxide sol particles, when the slurry is spray dried the solute particles can flow with the solvent from the interior to the peripheral region of the porous microsphere formed by the evaporation of the solvent in a droplet of the spray. These solute particles then remain in this peripheral region as the drying is completed and form a hard peripheral shell.

The oxide for this shell can be chosen from the group comprising $SiO_2$, $Al_2O_3$, $P_2O_5$, $TiO_2$, $ZrO_2$, MgO, and rare earth oxides. Examples of solutes for these oxides are silicic acid, basic aluminum chloride, phosphoric acid, titanyl oxychloride, hydrolyzed zirconyl nitrate, magnesium acetate, and hydrolyzed basic nitrates of rare earths. The preferred oxide is $SiO_2$, and the preferred solute or oxide precursor is silicic acid, especially polysilicic acid.

The aqueous silicic acid solution that is useful in this invention contains silica of the proper particle size, i.e., no greater than 5 nm, and provides a solution of sufficient stability to allow the formation of the slurry and subsequent spray drying. The silicic acid can be in the form of a monomer or in the form of low molecular weight polymeric units. It is a very weak acid and exists only in dilute aqueous solutions. At greater concentrations, the monomer polymerizes to form dimer and higher molecular weight species of silicic acid.

The preferred form of silicic acid is polysilicic acid having a concentration expressed as $SiO_2$ of about 6 wt % for adequate stability. The preferred method of preparation of polysilicic acid is by deionization of an aqueous sodium silicate solution using an ion exchange resin at room temperature. In this way the polysilicic acid solution is substantially free of electrolytes and, therefore, is more stable. Further details and alternatives are described in previously referenced U.S. Pat. Nos. 4,677,084 and 4,769,477.

The slurry which is spray dried is prepared by gradually adding catalyst or catalyst precursor particles to an aqueous mixture of a $H_3PO_4$ solution, and the colloidal sol and silicic acid solutions. The slurry is stirred until a uniform dispersion is obtained. Preferably the relative amounts of colloidal sol, silicic acid, and catalytic particles are chosen so that the resulting weight of the $SiO_2$ represents from about 3 to 15 percent of the total weight of the attrition resistant catalyst.

The spray drying and calcining steps can be performed by any of the known processes and equipment generally known in the art. In particular these steps may be performed in a manner similarly to the disclosure in U.S. Pat. Nos. 4,677,084 and 4,769,477.

The following examples are presented to more fully demonstrate and further illustrate various individual aspects and features of the present invention. As such the examples are felt to be non-limiting and are meant to illustrate the invention but are not meant to be limiting in any way.

EXAMPLE 1

An attrition resistant VPO catalyst having a shell and/or bulk composition of 10% SiO2 has been prepared.

To (Y grams) of colloidal silica sol (X) having an average particle size (S) with pH (P) was added a strongly acidic sulfonic acid cation exchange resin (Dowex HCR-W2-H) until the pH was <3.00. The deionized colloid (X) was then separated from the resin by filtration.

A 6.13% by weight sodium silicate solution was prepared by diluting sodium silicate (N Grade; Wesbond Corp.) with distilled water. The pH was lowered to <3.00 by the addition of Dowex HCR-W2-H resin, then stabilized with 6.9% Sulfuric Acid, and the resin was removed by filtration.

The catalyst precursor particles employed were milled hydrogen vanadyl phosphate having a mean particle diameter d50 of (2.0) microns.

A slurry was prepared from (V grams) of the milled VPO precursor particles, (Y grams) of the deionized colloid (X), (Y grams) of the 6.13% by weight PSA solution, (Z Grams) of water, and (F Grams) of 85% Phosphoric Acid ($H_3PO_4$), by first mixing the aqueous solutions then the VPO precursor particles to form a slurry. The slurry was spray dried on a Bowen Engineering Inc. spray dryer, Model # BE-1425.

The conditions for spray drying were:

| | | |
|---|---|---|
| Inlet temp: | 370 ± 5 | |
| Outlet temp: | | 175 ± 5 |
| Atomizer air: | | 8 psi ± 2 |
| Cyclone ΔP in H20: | 4.5 ± 5 | |
| Chamber temp: | | 245° C. ± 5 |

Calcination and activation was carried out in the following manner: 90 g of spray dried VPO/SiO2 material was loaded into a 4 cm diameter fluid bed. The 90 g of VPO catalyst was fluidized with air and heated to 390 C° for 1 hr. After this calcination step, the VPO catalyst was activated with 1.5% butane at 460 C° for approximately 14 hours.

EXAMPLE 2

An attrition resistant VPO catalyst having a shell and/or bulk composition of 10% SiO2 has been prepared.

To a mixture of, (Y grams) of colloidal silica sol (X) having an average particle size (S) with pH (P), a 6.13% by weight sodium silicate solution prepared by diluting sodium silicate (N Grade; Wesbond Corp.) with distilled water, and (F Grams) of 85% Phosphoric Acid ($H_3PO_4$), was added a strongly acidic sulfonic acid cation exchange resin (Dowex HCR-W2-H) until the pH was <3.00. The deionized mixture was then separated from the resin by filtration.

The catalyst precursor particles employed were milled hydrogen vanadyl phosphate having a mean particle diameter d50 of (2.0) microns.

A slurry was prepared from (V grams) of the milled VPO precursor particles, (Y grams) of the deionized colloid (X), (Y grams) of the 6.13% by weight PSA solution, (Z Grams) of water, and (F Grams) of $H_3PO_4$, by adding the VPO precursor particles to the aqueous mixture to form a slurry. The slurry was spray dried on a Bowen Engineering Inc. spray dryer, Model # BE-1425.

The conditions for spray drying were:

| | | |
|---|---|---|
| Inlet temp: | 370 ± 5 | |
| Outlet temp: | | 175 ± 5 |
| Atomizer air: | | 8 psi ± 2 |
| Cyclone ΔP in H20: | 4.5 ± 5 | |
| Chamber temp: | | 245° C. ± 5 |

Calcination and activation was carried out in the following manner: 90 g of spray dried VPO/$SiO_2$ material was loaded into a 4 cm diameter fluid bed. The 90 g of VPO catalyst was fluidized with air and heated to 390 C° for 1 hr. After this calcination step, the VPO catalyst was activated with 1.5% butane at 460 C° for approximately 14 hours.

EXAMPLE 3

An attrition resistant VPO catalyst having a shell and/or bulk composition of 10% $SiO_2$ has been prepared.

To (Y grams) of colloidal silica sol (X) having an average particle size (S) with pH (P) was added a strongly acidic sulfonic acid cation exchange resin (Dowex HCR-W2-H) until the pH was <3.00. The deionized colloid (X) was then separated from the resin by filtration.

The catalyst precursor particles employed were milled hydrogen vanadyl phosphate having a mean particle diameter d50 of (2.0) microns.

A slurry was prepared from (V grams) of the milled VPO precursor particles, (Y grams) of the deionized colloid (X), (Z Grams) of water, and (F Grams) of 85% Phosphoric Acid ($H_3PO_4$), by first mixing the aqueous solutions then the VPO precursor particles to form a slurry. The slurry was spray dried on a Bowen Engineering Inc. spray dryer, Model # BE-1425.

The conditions for spray drying were:

| | |
|---|---|
| Inlet temp: | 370 ± 5 |
| Outlet temp: | 175 ± 5 |
| Atomizer air: | 8 psi ± 2 |
| Cyclone ΔP in H20: | 4.5 ± 5 |
| Chamber temp: | 245° C. ± 5 |

Calcination and activation was carried out in the following manner: 90 g of spray dried VPO/$SiO_2$ material was loaded into a 4 cm diameter fluid bed. The 90 g of VPO catalyst was fluidized with air and heated to 390 C° for 1 hr. After this calcination step, the VPO catalyst was activated with 1.5% butane at 460 C° for approximately 14 hours.

EXAMPLE 4

An attrition resistant VPO catalyst having a shell and/or bulk composition of 10% $SiO_2$ has been prepared.

The catalyst precursor particles employed were milled hydrogen vanadyl phosphate having a mean particle diameter d50 of (2.0) microns.

A slurry was prepared from (V grams) of the milled VPO precursor particles, (Z Grams) of water, and (F Grams) of 85% Phosphoric Acid ($H_3PO_4$), by first mixing the aqueous solutions then the VPO precursor particles to form a slurry. The slurry was spray dried on a Bowen Engineering Inc. spray dryer, Model # BE-1425.

The conditions for spray drying were:

| | |
|---|---|
| Inlet temp: | 370 ± 5 |
| Outlet temp: | 175 ± 5 |
| Atomizer air: | 8 psi ± 2 |
| Cyclone ΔP in H20: | 4.5 ± 5 |
| Chamber temp: | 245° C. ± 5 |

Calcination and activation was carried out in the following manner: 90 g of spray dried VPO/$SiO_2$ material was loaded into a 4 cm diameter fluid bed. The 90 g of VPO catalyst was fluidized with air and heated to 390 C° for 1 hr. After this calcination step, the VPO catalyst was activated with 1.5% butane at 460 C° for approximately 14 hours.

In A manner analogous to the above Examples, a series of additional runs or partial runs were performed including various selected colloidal sol particle sizes, polysilic acid concetrations and $H_3PO_4$/$H_2SO_4$ concentrations. The relevant starting data and results of the respective runs including data are presented in the following Tables.

| | | | | Oxide Product Name (X) | | | | | | | | |
|---|---|---|---|---|---|---|---|---|---|---|---|---|
| | | PSA | Ludox FM | Ludox SM | Nalco 1115 | Nalco 1034A | Nalco 1060 | Nalco 2329 | | | | |
| | | | | Dry Oxide % | | | | | | | | |
| | | 6.13% SiO2 | 15% SiO2 | 30% SiO2 | 15% SiO2 | 34% Sio2 | 50% SiO2 | 40% SiO2 | | | | |
| | | | | Particle Size (S) | | | | | | | | |
| | | N/A | 50 A | 70 A | 40 A | 200 A | 600 A | 750 A | | | | |
| | | | | pH (P) | | | | | | | | |
| | | <3.00 | 9.7> <10.3 | 10 | 10.5 | 2.8 | 8.5 | 8.4 | VPO | WATER | H3PO4 | H2SO4 |
| Run # | Ex. | | | Oxide weight, g (Y) | | | | | g (V) | g (Z) | g (F) | ml (A) |
| 5 | 1 | 91.0 | 704.0 | | | | | | 1000.0 | 982.8 | 8.4 | 3.0 |
| 6 | 1 | 90.7 | | | | | 211.1 | | 1000.0 | 1476.0 | 8.4 | 1.5 |
| 7 | 1 | 42.9 | | | | | 100.0 | | 1000.0 | 1556.1 | 8.2 | 1.5 |
| 8 | 2 | 90.0 | | 352.0 | | | | | 1000.0 | 1407.0 | 8.7 | 0.0 |
| 9 | 2 | 90.0 | | 352.0 | | | | | 1000.0 | 1407.0 | 8.7 | 0.0 |
| 10 | 2 | 90.0 | | 352.0 | | | | | 1000.0 | 1407.0 | 8.7 | 0.0 |
| 11 | 3 | | | | | | 222.2 | | 1000.0 | 1555.6 | 8.4 | 0.0 |
| 12 | 3 | | | | | | | 277.8 | 1000.0 | 1500.0 | 8.4 | 0.0 |
| 13 | 3 | | | | | 326.8 | | | 1000.0 | 1451.0 | 8.4 | 0.0 |
| 14 | 3 | | | | 370.4 | | | | 1000.0 | 1407.4 | 8.4 | 0.0 |
| 15 | 3 | | 740.7 | | | | | | 1000.0 | 1037.1 | 8.4 | 0.0 |
| 16 | 3 | | | | | | 222.2 | | 1000.0 | 1555.6 | 16.8 | 0.0 |
| 17 | 3 | | | | 370.4 | | | | 1000.0 | 1407.4 | 16.8 | 0.0 |
| 18 | 3 | | | | | | 222.2 | | 1000.0 | 1555.6 | 8.4 | 0.0 |
| 19 | 3 | | | | | | 222.2 | | 1000.0 | 1555.6 | 8.4 | 0.0 |
| 20 | 3 | | | | | | 222.2 | | 1000.0 | 1555.6 | 8.4 | 0.0 |
| 21 | 3 | | | | | | 222.2 | | 1000.0 | 1555.6 | 8.4 | 0.0 |
| 22 | 3 | | | | 370.4 | | | | 1000.0 | 1407.4 | 8.4 | 0.0 |

-continued

| | | Oxide Product Name (X) | | | | | | | | | |
|---|---|---|---|---|---|---|---|---|---|---|---|
| | PSA | Ludox FM | Ludox SM | Nalco 1115 | Nalco 1034A | Nalco 1060 | Nalco 2329 | | | | |
| | | | | Dry Oxide % | | | | | | | |
| | 6.13% SiO2 | 15% SiO2 | 30% SiO2 | 15% SiO2 | 34% Sio2 | 50% SiO2 | 40% SiO2 | | | | |
| | | | | Particle Size (S) | | | | | | | |
| | N/A | 50 A | 70 A | 40 A | 200 A | 600 A | 750 A | | | | |
| | | | | pH (P) | | | | | | | |
| Run # | Ex. | <3.00 | 9.7> <10.3 | 10 | 10.5 | 2.8 | 8.5 | 8.4 | VPO g (V) | WATER g (Z) | H3PO4 g (F) | H2SO4 ml (A) |
| | | | | Oxide weight, g (Y) | | | | | | | |
| 23 | 3 | | | 370.4 | | | | | 1000.0 | 1407.4 | 8.4 | 0.0 |
| 24 | 3 | | | 370.4 | | | | | 1000.0 | 1407.4 | 8.4 | 0.0 |
| 25 | 3 | | | 370.4 | | | | | 1000.0 | 1407.4 | 8.4 | 0.0 |
| 26 | 3 | | | | | | 888.9 | | 4000.0 | 6222.4 | 67.2 | 0.0 |
| 27 | 3 | | | | | | | 105.3 | 1000.0 | 1526.3 | 15.7 | 0.0 |
| 28 | 3 | | | 175.0 | | | | | 1000.0 | 1524.0 | 8.2 | 0.0 |
| 29 | 3 | | | 370.4 | | | | | 1000.0 | 1478.6 | 8.7 | 0.0 |
| 30 | 4 | 0.0 | 0.0 | 0.0 | 0.0 | 0.0 | 0.0 | 0.0 | 1000.0 | 1500.0 | 14.7 | 0.0 |
| 31 | 4 | 0.0 | 0.0 | 0.0 | 0.0 | 0.0 | 0.0 | 0.0 | 4000.0 | 6256.0 | 76.6 | 0.0 |

| | | | | | VPO/OXIDE %'S | | | | | | | |
|---|---|---|---|---|---|---|---|---|---|---|---|---|
| Run # | PSA | 50 A Ludox FM | 70 A Ludox SM | 40 A Nalco 1115 | 200 A Nalco 1034A | 600 A Nalco 1060 | 750 A Nalco 2329 | H3PO4 mMol | g/hr Attri. | SA m2/mg | Pore Vol. cc/g | Description |
| 11 | | | | | | | | 50 | 1.670 | | | 10% SiO2/H3PO4 |
| 12 | | | | | | | | 50 | 0.132 | | | 10% SiO2/H3PO4 |
| 13 | | | | | | | | 50 | 0.050 | | | 10% SiO2/H3PO4 |
| 5 | 5% | 95% | | | | | | 50 | 0.023 | 31.31 | 0.13 | 10% SiO2/H3PO4 |
| 14 | | | 100% | | | | | 50 | | | | 10% SiO2/H3PO4 |
| 15 | | 100% | | | | | | 50 | | | | 10% SiO2/H3PO4 |
| 30 | 0% | 0% | 0% | 0% | 0% | 0% | 0.00 | 100 | 0.045 | 34.80 | 0.18 | 100% VPO/H3PO4 (No SiO2!!) |
| 16 | | | | | | 100% | | 100 | 0.018 | 42.73 | 0.22 | 10% SiO2/H3PO4 |
| 17 | | | 100% | | | | | 100 | 0.232 | | | 10% SiO2/H3PO4 |
| 18 | | | | | | 100% | | 50 | 0.018 | | | 10% SiO2/H3PO4, t = 0 hr |
| 19 | | | | | | 100% | | 50 | | | | 10% SiO2/H3PO4, t = 1 hr |
| 20 | | | | | | 100% | | 50 | | | | 10% SiO2/H3PO4, t = 3 hrs |
| 21 | | | | | | 100% | | 50 | 0.023 | | | 10% SiO2/H3PO4, t = 5 hrs |
| 22 | | | 100% | | | | | 50 | 0.008 | | | 10% SiO2/H3PO4, t = 0 hr |
| 23 | | | 100% | | | | | 50 | | | | 10% SiO2/H3PO4, t = 1 hr |
| 24 | | | 100% | | | | | 50 | | | | 10% SiO2/H3PO4, t = 3 hrs |
| 25 | | | 100% | | | | | 50 | 0.009 | | | 10% SiO2/H3PO4, t = 5 hrs |
| 26 | | | | | | 100% | | 100 | 0.028 | | | 10% SiO2 (riser repeat 88545-19) |
| 27 | | | | | | | 100% | 100 | | | | 5% SiO2/H3PO4 |
| 31 | 0% | 0% | 0% | 0% | 0% | 0% | 0.00 | 125 | 0.077 | 31.41 | 0.14 | 100% new VPO (¼" repet 88545-18) |
| 32 | 5% | 95% | | | | | | 50 | 0.011 | | | 10% SiO2/premix/H3PO4, t = 0 hr |
| 33 | 5% | 95% | | | | | | 50 | 0.018 | | | 10% SiO2/premix/H3PO4, t = 5 hrs |
| 34 | 5% | 95% | | | | | | 50 | 0.011 | | | 10% SiO2/premix/H3PO4, t = 24 hrs |
| 28 | | 100% | | | | | | 50 | 0.095 | | | 5% SiO2/H3PO4 |
| 29 | | 100% | | | | | | 50 | 0.013 | | | 10% SiO2/H3PO4 |
| 6 | 5% | | | | | | | 50 | 0.178 | 32.17 | 0.15 | 10% SiO2/H3PO4 |
| 7 | 5% | | | | | | | 50 | 0.053 | | | 5% SiO2/H3PO4 |

Having thus described and exemplified the invention with a certain degree of particularity, it should be appreciated that the following claims are not to be so limited but are to be afforded a scope commensurate with the wording of each element of the claim and equivalents thereof.

We claim:

1. Process for manufacture of an attrition resistant vanadium/phosphorous oxide catalyst comprising the steps of:
   a) forming a slurry comprising;
      i) vanadium/phosphorous oxide catalyst or vanadium/phosphorous oxide catalyst precursor particles,
      ii) aqueous $H_3PO_4$ solution having a concentration of 50 to 125 millimolar, and
      iii) optionally an aqueous colloidal silica sol, an aqueous polysilicic acid solution or mixture thereof;
   b) spray drying the slurry from step (a) to form attrition resistant catalyst precursor solids; and
   c) calcining the spray dried solids of step (b) to produce attrition resistant catalyst.

* * * * *